United States Patent [19]

Seshimoto et al.

[11] Patent Number: 4,732,849
[45] Date of Patent: Mar. 22, 1988

[54] MULTILAYERED CHEMICAL ANALYSIS MATERIAL FOR ANALYSIS OF AQUEOUS LIQUIDS

[75] Inventors: Osamu Seshimoto; Masao Kitajima, both of Saitama, Japan

[73] Assignee: Fuji Photo Film Co., Ltd., Kanagawa, Japan

[21] Appl. No.: 828,562

[22] Filed: Feb. 10, 1986

Related U.S. Application Data

[63] Continuation of Ser. No. 600,220, Apr. 17, 1984, abandoned, which is a continuation of Ser. No. 206,604, Nov. 13, 1980, abandoned.

[30] Foreign Application Priority Data

Nov. 13, 1979 [JP] Japan ................................ 54-146000

[51] Int. Cl.$^4$ ............................................ C12Q 1/58
[52] U.S. Cl. .................................... 435/12; 435/805; 422/56
[58] Field of Search .................. 436/108, 170; 422/56, 422/57, 69; 23/924; 435/805, 12; 424/7

[56] References Cited

U.S. PATENT DOCUMENTS

| | | | |
|---|---|---|---|
| 3,119,751 | 1/1964 | Chaney | 435/12 |
| 3,395,082 | 7/1968 | Mast | 435/12 |
| 3,873,269 | 3/1975 | Kraffczyk et al. | 435/12 |
| 4,066,403 | 1/1978 | Bruschi | 435/12 |
| 4,101,382 | 7/1978 | Chang | 435/12 |
| 4,176,008 | 11/1979 | Figueras et al. | 435/12 |
| 4,248,973 | 2/1981 | Kallies | 435/12 X |
| 4,255,384 | 3/1981 | Kitajima et al. | 422/56 X |
| 4,256,693 | 3/1981 | Kondo et al. | 435/805 X |
| 4,270,920 | 6/1981 | Kondo et al. | 23/924 X |

OTHER PUBLICATIONS

Hackh's Chemical Dictionary; 4th Ed.; 1969; edited by J. Grant; McGraw-Hill Book Co., N.Y., p. 378.

Primary Examiner—Kenneth M. Schor
Attorney, Agent, or Firm—Sughrue, Mion, Zinn, Macpeak & Seas

[57] ABSTRACT

A multi-layered, chemical analysis material for analysis of an aqueous liquid, which comprises in one embodiment (a) a light-transmitting, water-impermeable support having provided thereon in sequence
(b) a reagent layer and
(c) a porous, sample-spreading layer, with
  (i) the reagent layer (b) containing a lake dye precursor dispersed in a hydrophilic binder,
  (ii) urease incorporated in the reagent layer (b) or in a layer adjacent the reagent layer (b), and
  (iii) a lake forming metal salt or lake forming metal oxide, which does not substantially inhibit the activity of urease, incorporated in the reagent layer (b) or in a layer adjacent the reagent layer (b) or a lake forming metal salt or oxide incorporated in a layer adjacent the reagent layer (b); and in a second embodiment the chemical analysis material includes
(d) a radiation-blocking layer interposed between said reagent layer (b) and said porous, sample-spreading layer (c).

44 Claims, 3 Drawing Figures

MULTILAYERED CHEMICAL ANALYSIS MATERIAL FOR ANALYSIS OF AQUEOUS LIQUIDS

This is a continuation, of application Ser. No. 600,220 filed Apr. 17, 1984 which is a continuation of U.S. Ser. No. 206,604, filed Nov. 13, 1980 (all in the name of Seshimoto et al) both being now abandoned.

FIELD OF THE INVENTION

This invention relates to a multi-layered, chemical analysis material for use in analysis of an aqueous liquid sample to determine a specific component contained therein. The chemical analysis material comprises a support, a reagent layer, and a sample-spreading layer, or comprises a support, a reagent layer, a radiation-blocking layer and a sample-spreading layer. More particularly, in the chemical analysis material the reagent layer contains a lake dye precursor dispersed in a hydrophilic binder, urease is present in the reagent layer or in a layer adjacent thereto, and a lake forming metal salt or lake forming metal oxide, which does not substantially inhibit the activity of the urease, is incorporated in the reagent layer or in a layer adjacent thereto, or a layer containing the lake forming metal salt or lake forming metal oxide is independently provided adjacent the reagent layer.

BACKGROUND OF THE INVENTION

As to multi-layered, chemical analysis materials (sheet form) enabling analysis through dry processes, those which comprise a support having provided thereon in sequence a single- or double-layered reagent layer and a non-fibrous, isotropic, sample-spreading layer are known as described, for example, in Japanese Patent Publication No. 33800/74 (corresponding to U.S. Pat. No. 3,630,957), Japanese Patent Application (OPI) Nos. 53888/74 (corresponding to U.S. Pat. No. 3,992,158), 137192/75 (corresponding to U.S. Pat. No. 3,977,568), 40191/76 (corresponding to U.S. Pat. No. 4,042,335), 3488/77 (corresponding to U.S. Pat. No. 4,066,403), 89796/78 (corresponding to U.S. Pat. No. 4,069,017), and 131089/78 (corresponding to U.S. Pat. No. 4,144,306). When an aqueous liquid sample is applied to the sample-spreading layer of these materials, the aqueous liquid sample migrates into the reagent layer with a uniform concentration, and causes a color-forming reaction to occur there. The changes in color density which occurs enables the concentration or level of a certain component in the aqueous liquid sample to be determined.

In determining a certain component in an aqueous liquid, a single reagent very often can not be employed for the chemical analysis and, in may cases, several reagents are used in combination. For example, in determining urea in blood, a direct determination of urea with a single reagent ordinarily is not used. Generally, urea is determined through several step reactions; for example, urea is first enzymatically decomposed with a first reagent, urease, to produce ammonia, and the ammonia is in turn brought into contact with a second reagent, for example, a pH indicator or a mixture of a diazonium salt and a coupler, thus eventually the presence of urea being determined through the dye formation system.

Multi-layered, analysis sheets using a plurality of reagents for multi-step reactions as described above include those wherein all necessary reagents can be incorporated in a single reagent layer, and those where the reagents are conveniently separated into a primary reagent and a secondary reagent depending on the order of the reactions, each of which reagents is incorported in, or forms, a different reagent layer.

Furthermore, multi-layered, chemical analysis sheets described in U.S. Pat. No. 3,011,874 and Japanese Patent Application (OPI) No. 3488/77 have a complicated multi-layered structure wherein reagents are incorporated separately into two layers, with one reagent layer using a hydrophobic binder or covered with a hydrophobic membrane for protection against permeation of water. Thus, reactions for determining an component in an aqueous liquid sample are clearly separated into two stages—first, aqueous reaction; then, non-aqueous reaction.

Multi-layered, chemical analysis sheets having the above-described multi-layered construction are generally prepared by repeating the steps of coating of a hydrophilic binder layer on a hydrophobic binder layer. This often results in delamination due to weak adhesion between the two layers. Therefore, in practice, at least one adhesive layer, called an subbing layer or an interlayer, is provided on the hydrophobic binder layer, followed by providing thereon the hydrophilic binder layer. Thus, to provide a reagent layer as two layers, a hydrophobic layer and a hydrophilic layer, requires production steps which are quite complicated.

In an analysis procedure for determining a specific component in an aqueous solution sample, which requires a plurality of reagents separated into two or more groups and one group of reagents to react in a hydrophilic environment and the other group of reagents in a non-aqueous environment, conventionally well known techniques utilize multi-layered, chemical analysis materials having a complicated construction wherein the reagents are incorporated separately in a hydrophilic binder layer and a hydrophobic binder layer. On the other hand, in the multi-layered chemical analysis material of the present invention for analyzing an aqueous liquid sample the reagent layer of the analysis material has a single- or multi-layered structure supported by a hydrophilic binder. Thus the coating and, therefore, production steps are simplified.

SUMMARY OF THE INVENTION

An object of the present invention is to provide a multi-layered, chemical analysis material for analysis of an aqueous liquid, which comprises in one embodiment (a) a light-transmitting, water-impermeable support having provided thereon in sequence (b) a reagent layer, and (c) a porous, sample-spreading layer, with
  (i) the reagent layer (b) containing a lake dye precursor dispersed in a hydrophilic binder,
  (ii) urease incorporated in the reagent layer (b) or in a layer adjacent the reagent layer (b) and
  (iii) a lake forming metal salt or lake forming metal oxide, which does not substantially inhibit the activity of the urease, incorporated in the reagent layer (b) or in a layer adjacent the reagent layer (b), or a lake forming metal salt or lake forming metal oxide incorporated in a layer provided adjacent the reagent layer (b).

In a further embodiment of this invention, this invention provides a chemical analysis material as described above including additionally (d) a radiation-blocking layer interposed between the reagent layer (b) and the porous, sample-spreading layer (c).

DETAILED DESCRIPTION OF THE INVENTION

Figure 1:
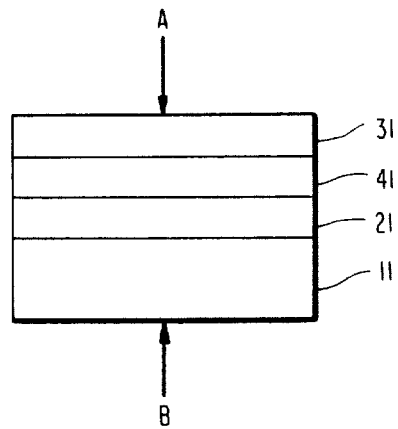
FIGS. 1 to 3 are schematic views showing stratum structures of specific examples of the multi-layered, chemical analysis materials of the present invention for use in analysis of an aqueous liquid.

The substantially single-layered structure of the reagent layer of the chemical analysis material of the present invention simplifies the coating step as described above, as compared with that for conventional multi-layered materials and, since aqueous coating is permitted, the production cost is reduced and excellent safety is achieved. Further, fading, which occurs with conventional materials and is a serious defect with conventional detection methods using a pH indicator, is eliminated or markedly reduced with the chemical analysis material of the present invention. A color which does not change with time and excellent light fading resistance with a stable color tone are achieved in the chemical analysis material of this invention. Thus stable analysis performance with high accuracy is achieved using such. The chemical analysis material of the present invention is particularly suited for treatment with large quantity.

The multi-layered, chemical analysis material of the present invention for use in analysis of an aqueous liquid is designed to be used for the analysis of a liquid sample, in particular urea in body fluids. Body fluids, blood, urine, spinal fluid, saliva, etc. are usually subjected to analysis, and the multi-layered, chemical analysis material of the present invention is effective for analysis of any of these fluids. Of these body fluids, analysis of blood is particularly important. Blood urea nitrogen (BUN) is frequently employed as a diagnostic item for checking renal function.

Various methods have heretofore been developed and put into practice for measurement of BUN but, in such methods, liquids to be analyzed are in many cases blood serum or blood plasma, with the reaction being conducted in a dilute solution.

The method using the multi-layered, chemical analysis material of the present invention for analyzing an aqueous liquid does not require use of any diluent, that is, such can be considered to be dry chemistry, and it is a means for analyzing an aqueous liquid with an extremely high accuracy.

The chemical analysis material of the present invention can be used to analyze not only blood serum or plasma but also whole blood as a liquid for direct analysis by combining the techniques disclosed in Japanese Patent Application No. 83608/79, corresponding to U.S. patent application Ser. No. 165,444, filed July 2, 1980, the disclosure of which applications is herein incorporated by reference. When whole blood as a liquid is analyzed, too, the measurement procedures are exactly the same as in the case of analysis of blood serum or plasma, and all that is required is to spot a slight amount (e.g., 5 to 20 $\mu$l) of whole blood on the chemical analysis material. Procedures for the removal of erythrocytes, such as washing or wiping off after spotting whole blood, which are considered to be necessary with respect to test paper type analysis sticks, are not necessary at all with the chemical analysis material of this invention.

In measuring the level of urea in body fluids, particularly blood, in the past a pH indicator has been used and the change in pH upon decomposition of urea to ammonia by urease is noted. In this case, however, the thus produced ammonia escapes out of the system due to vaporization or the like, with fading or disappearance of indicated color occurring. This makes an accurate determination of urea difficult.

The chemical analysis material of the present invention solves the above-described problem. In the case of using, for example, haematoxylin as a lake dye precursor, a change from a colorless state to a reddish violet state occurs due to the action of alkali but, if maintained as such, the thus formed color gradually fades. However, when an oxidation reaction effectively takes place in parallel, red haematein is formed. In this situation, with the copresence of a metal salt described in this specification such as iron sodium ethylenediaminetetraacetate (EDTA.Fe (III).Na) or the like a blue-violet lake is formed. The color of this lake never disappears, and hence the urea level can be accurately measured. Furthermore, since the dye once formed using the chemical analysis material of the present invention is insoluble, the so-called ringing phenomenon is controlled and thus accuracy is improved.

Suitable light-transmitting, water-impermeable supports for the multi-layered, chemical analysis material of the present invention which can be used for analyzing an aqueous liquid include known supports having a thickness of about 50 $\mu$m to about 2 mm, preferably 80 to 300 $\mu$m. Such a support is considered light-transmitting if transparent to visible and near ultraviolet light, e.g. with a wavelength of about 290 mm to 400 mm. Suitable examples include synthetic resin films such as polyesters or polycarbonates (e.g., polyethylene terephthalate or polycarbonates of bisphenol A, cellulose esters (e.g., cellulose diacetate, cellulose triacetate, cellulose acetate propionate, etc.), polymethyl methacrylate, etc., regenerated cellulose and glass plates. With hydrophobic supports which result in insufficient adhesion with the hydrophilic binder of the reagent layer, known auxiliary treatments such as rendering the support surface hydrophilic (for example, irradiation with ultraviolet light, irradiation with electron beams, flame treatment, hydrolysis with alkali, etc.) formation of a subbing layer comprising a material which has a suitable adhesion to both of the support and the hydrophilic binder of reagent layer on the surface of the support, and formation of fine unevenness on the support surface to the degree that light-transmitting properties are not seriously reduced (for example, brushing, electrolytic etching, etc.) can be used. Further, suitable light-transmitting, water-impermeable supports which can be used include those supports which are prepared by previously coating a mordanting polymer layer on the above-described support. Colorless, transparent supports are generally used. However, in order to facilitate observation or measurement of the coloration or discoloration reaction in the reagent layer and to increase the contrast to improve the accuracy of the observation or measurement, colored transparent supports may also be used in the chemical analysis material of the present invention.

Suitable porous, sample-spreading layers which can be used in the multi-layered chemical analysis material of the present invention include fabrics, preferably which have been subjected to a treatment to render such hydrophilic. Examples of fabrics rendered hydrophilic, include fabric sufficiently degreased by washing and then drying, and fabrics impregnated, after being degreased by washing, with small amounts of a surfactant, a wetting agent, and a hydrophilic polymer which contain or which does not contain $TiO_2$ or $BaSO_4$ fine powder dispersed therein. The techniques and fabrics to be employed to render the fabric hydrophilic as the porous, sample-spreading layer are specifically described in detail in Japanese Patent Application No. 72047/79, corresponding to U.S. patent application Ser. No. 157,735, filed June 9, 1980, of the present inventors, the disclosure of which applications is incorporated by reference, and can be applied to the description therein. The porous, sample-spreading layer can have a thickness of about 80 μm to about 1 mm, preferably about 100 μm to about 400 μm, in terms of the thickness after such is rendered hydrophilic and dried naturally. Further, the fabrics which can be used may be knitted or woven, and suitable examples of fabrics which can be used include fabrics composed of natural fibers, fabrics of mixed yarns of natural fibers and synthetic polymers, and fabrics composed of synthetic polymers.

Where the porous, sample-spreading layer comprises fabric rendered hydrophilic, the sample-spreading layer can be provided by bonding the hydrophilic fabric onto the reagent layer.

Methods for bonding the hydrophilic fabric onto the reagent layer which can be employed include a method of closely contacting the hydrophilic fabric with the surface of the reagent layer while the reagent layer is semi-dried or while the surface of the reagent layer is wet with water or with water containing a surfactant such as a non-ionic surfactant, and, if necessary, applying a suitable pressure to the assembly, thus utilizing the properties of the hydrophilic binder polymer of the reagent layer. As an alternative method for bonding the hydrophilic fabric onto the reagent layer, a method using an adhesive through which an aqueous liquid sample can be passed and a method of providing an adhesive layer through which an aqueous liquid sample can be passed, as described hereinafter, on the reagent layer can be used.

Further, non-fibrous, isotropic, porous materials as described in Japanese Patent Application (OPI) Nos. 53888/74, 137192/75, etc. can also be used as the porous, sample-spreading layer.

In analyzing blood as a liquid to be analyzed with the multi-layered, chemical analysis material of the present invention, any of whole blood, blood serum, and blood plasma can be used when the proous, sample-spreading layer is formed by a layer which has been rendered hydrophilic. However, when the porous, sample-spreading layer is formed of a non-fibrous, isotropic material, only blood serum and blood plasma can be used, and this material is not appropriate for analysis of whole blood.

The lake dye precursors incorporated in the reagent layer of the multi-layered, chemical analysis material of the present invention include compounds which irreversibly form a dye in the copresence of a lake forming metal salt or lake forming metal oxide under ammoniacally alkaline conditions.

These lake dye precursors are those compounds which have groups capable of interacting with metals, such as —OH, —SH and/or C=O, C=S, =N—R (where R is an organic group), —NH₂, etc. groups, in their structure before reaction with ammonia or those which, after reaction with ammonia (if necessary, oxygen being present), form a structure containing the above-described reactive groups.

Examples of lake dye precursors particularly desirable for use in the present invention, include those which do not substantially deteriorate the activity of the ammonia-releasing enzyme, urease, in the course of mixing, coating and drying steps in the copresence of urease using a hydrophilic polymer as a binder, and which are not colored upon being dried. Specific examples of such lake dye precursors include haematoxylin, brazilin, dithizone, diphenylcarbazide, oxine, rubeanic acid, formaldoxime, dimethylglyoxime, alizarin, sodium rhodinate, etc. Of these specific examples of lake dye precursors, haematoxylin is particularly preferred. While many other dye precursors are quite colored in the copresence of a metal salt even in the absence of ammonia, haematoxylin is not colored at all even in the copresence of $TiO_2$ by controlling the pH, and thus fogging is minimized. Furthermore, the excellent compatibility of haematoxylin with gelatin, one of the hydrophilic binders to be described hereinafter, enables aqueous coating to be conducted. Other examples than haematoxylin that undergo less coloration include oxine, dimethylglyoxime, etc. These have a poor solubility in water, and hence they are preferably used by dispersing them using emulsification.

The pH range where the coloration reaction occurs in the chemical analysis material of the present invention is desirably about 6.5 or higher, and hence dyes having a color change point at pH 5 or less are difficult to use from a practical standpoint.

The multi-layered, chemical analysis material of the present invention for analyzing aqueous liquids contains a urea-decomposing enzyme, urease, as a necessary component in analyzing urea. Urea in body fluids is decomposed into ammonia and carbon dioxide by urease. The principle of chemical analysis using the multi-layered, chemical analysis material of the present invention is as follows. Urea in body fluids is determined by utilizing the coloration reaction between the lake dye precursor and the lake-forming metal which occurs in proportion to the amount of ammonia produced by the above-described decomposition of urea by urease. Urease can be incorporated in the reagent layer or a layer adjacent thereto. Urease may be incorporated in a layer which is not adjacent the reagent layer. However, as is stated above, the coloration reaction proceeds in proportion to the amount of ammonia fed to the reagent layer and, when urease is incorporated in a layer apart from the reagent layer, coloration reaction efficiency, i.e., the urea-detecting sensitivity, is reduced in comparison with the case where the urease is incorporated in the reagent layer or in a layer adjacent thereto.

The amount of urease which can be used in the multi-layered, chemical analysis material of the present invention is about 50 to 5,000 Sumner units, preferably 100 to 1,000 Sumner units, per gram of the binder in the reagent layer or in the layer adjacent thereto.

Exemplary hydrophilic binders which can be used in the reagent layer include water-soluble high molecular weight polymers such as water-soluble proteins (e.g., gelatin, albumin, or collagen), vegetable gums (e.g., agar-agar, sodium alginate or agarose), and synthetic polymers (e.g., vinyl monomer-maleic anhydride copolymers in which the vinyl monomer can be ethylene, propylene, styrene, methyl methacrylate, etc., polyvinyl alcohol, polyvinyl pyrrolidone, polyacrylamide, poly(sodium vinylbenzenesulfonate, etc.), which can be used to form a film with the reagent therein and which, when dried, are capable of passing therethrough of an aqueous solution sample containing a component to be analyzed. The polymers described in R. L. Dazidson and M. Sittig, *Water-Soluble Resins*, 2nd Ed., Reinhold Book Corp., N.Y. (1968) can be suitably used as hydrophilic binders.

In the practice of the present invention, various additives are preferably added to the reagent layer or other layers for maintaining the activity of the urease. For example, stabilizers such as ethylenediaminetetraacetic acid (EDTA) and —SH group-containing compounds (e.g., mercapto-ethanol, cystine, glutathione, etc.) and various buffers for preventing fogging upon coating can be effectively incorporated into the reagent layer. Preferred examples of such additives include EDTA salts, phosphates, trishydroxyethylaminomethane hydrochloride, borates, etc. Coating is preferably conducted by buffering the coating composition at a pH of 5 or higher, more preferably 5.5 to 8.

The lake-forming metal salts or lake-forming metal oxides which can be used in the present invention include oxides or salts of multi-valent metals capable of irreversibly reacting with the lake dye precursors described above in the presence of ammonia to form stable dyes having a strong absorption in the visible region. Examples of metals constituting lake-forming metal salts or oxides which can be used are those which belong to Groups IIA, IIB, IIIB, IVA, IVB, VIA, VIIA, AND VIII in the Periodic Table.

It is well known that many metal ions belonging to the above-described groups inhibit the activity of urease. It has now been found that, even when salts or oxides composed of the above-described metals are present together with urease or when incorporated in an adjacent layer, the urease activity is substantially retained under certain conditions, thus achieving the present invention. The lake-forming metal salts or lake-forming metal oxides to be used in the present invention must exert essentially less inhibiting action on urease or must be slightly soluble with a low degree of coloration and, in the copresence of ammonia, must form a lake dye having a large molecular extinction coefficient by bonding with a lake dye precursor.

As a result of various investigations, $TiO_2$, $SiO_2$, $Al_2O_3$, and the double salts thereof with other metals, organic acid salts, complex salts, etc. have been found to be effective in the chemical analysis material of the present invention. Of these, $TiO_2$, $SiO_2$, EDTA salts, etc. are particularly effective. All EDTA salts are effective in the present invention. Particularly, the Fe(III) salt of EDTA is extremely effective, because a blue, slightly soluble lake dye is formed.

The reagent layer is formed by dispersing the lake dye precursor in hydrophilic binder, and coating the dispersion onto the support. The lake dye precursor can be employed in an amount of about 10 to 1,000 mg, preferably 50 to 500 mg, per gram of the binder of the reagent layer. In addition, the reagent layer preferably contains pH-buffering agents comprising EDTA salts, phosphates, borates, etc. These pH-buffering agents can be used in amounts of about 0.5 to 50 mM in terms of concentration in the coating solution. If necessary, surfactants, hardeners, antioxidants, stabilizers, toning agents, etc., may be incorporated into the reagent layer.

The lake dye precursor may be added to the reagent layer by dispersing such as fine particles, by emulsifying such and dispersing the emulsion as an organic solvent solution, by dispersing such as composite fine particles like microcapsules, or by dispersing such while supporting such on an inert solid through adsorption, as well as by dissolving such in a binder solution. Of these approaches, the method of preparing an organic solvent solution and emulsifying and dispersing such in an aqueous binder solution, described in detail in Japanese Patent Application No. 83608/79, is extremely effective in the present invention. This approach prevents fogging upon coating or drying and ensures coloration with high efficiency.

In the case of adding the multi-valent metal oxide or salt to be used for the formation of the lake dye to the reagent layer, a dissolving method and a dispersing method can be employed. The multi-valent metal salt or oxide can be used in amounts of about 5 to 500 mg, preferably 10 to 100 mg, per gram of the binder in the reagent layer.

A suitable dry thickness for the reagent layer is about 1 to 50 $\mu$m, preferably 5 to 30 $\mu$m.

The lake forming metal salt or lake forming metal oxide is incorporated in the reagent layer as described above and, in addition, it is also possible to independently provide a lake forming metal salt or oxide layer containing a multi-valent metal salt or oxide adjacent the reagent layer. In this case, the amount of lake forming metal salt or oxide may be the same as adding such to the reagent layer, or more than that amount can be used. That is, amounts of about 10 to 1,000 mg, preferably 10 to 100 mg, per gram of the hydrophilic binder in the reagent layer can be used. This layer may also contain pH-buffering salts, surfactants, stabilizers, etc. A suitable thickness for the lake forming metal salt or oxide layer is about 0.5 to 50 $\mu$m, preferably 1 to 20 $\mu$m. The multi-valent metal salt or oxide may be added by supporting such on an inert fine powder of glass or inorganic or organic material.

Furthermore, the lake forming metal salt or oxide may be present in a layer adjacent the reagent layer, this layer essentially having other functions such as a radiation-blocking or an adhesive layer.

In the multi-layered, chemical analysis material of the present invention for analyzing an aqueous liquid a radiation-blocking layer may be provided between the reagent layer and the porous, sample-spreading layer. Further, an adhesive layer through which an aqueous liquid sample can pass can be provided between the porous, sample-spreading layer and the reagent layer or the radiation-blocking layer for the purpose of strongly bonding the porous, sample-spreading layer. The radiation-blocking layer and the adhesive layer are described in detail in the previously cited Japanese and U.S. patent specifications and, in the present invention too, they can be provided according to the descriptions therein.

As the radiation-blocking layer, a layer of about 1 $\mu$m to about 50 $\mu$m, preferably about 2 $\mu$m to about 20 $\mu$m, in thickness, prepared by dispersing a fine white powder such as $TiO_2$ fine powder or $BaSO_4$ fine powder in a hydrophilic binder polymer, a layer of about 2 $\mu$m to about 50 $\mu$m, preferably about 2 $\mu$m to about 20 $\mu$m, in thickness formed by dispersing a white or slighty colored fine powder having a metallic luster such as aluminum in a hydrophilic binder polymer, or a porous metallic thin layer of about 5 nm to about 100 nm, preferably about 5 nm to about 50 nm, in thickness comprising a white or slightly colored metal such as aluminum and capable of passing an aqueous liquid sample therethrough can be employed.

Alternatively, the above-described powder may be incorporated into the porous, sample-spreading layer to thereby render to the porous, sample-spreading layer radiation blocking.

As the adhesive layer, a layer of a thickness of about 0.5 μm to about 10 μm, preferably about 0.7 μm to about 5 μm, which is composed of the same polymer as the aqueous sample-permeable hydrophilic polymer used as a binder in the reagent layer, radiation-blocking layer, etc., can be employed. In order to bond the adhesive layer composed of the hydrophilic polymer to the porous, sample-spreading layer, a hydrophilic polymer aqueous solution is coated on the reagent layer of the radiation-blocking layer and, while it is semi-dried with water or water containing a surfactant after being dried, fabric rendered hydrophilic is contacted with the surface, followed by applying an appropriate pressure to the assembly to uniformly bond such to the adhesive layer.

In the quantitative analysis of an aqueous sample using the multi-layered, chemical analysis material of the present invention, reflection density is often measured from the transparent support side. Accordingly, the lake dye is to be desirably produced on the side nearer the side from which measurement is made than the side of the radiation-blocking layer which scatters light. In particular, materials wherein the lake forming metal salt or oxide is present, together with the hydrophilic binder, as a coating layer under the reagent layer containing urease and the lake dye precursor are extremely advantageous from the standpoint of measuring reflection density, because formation of the lake dye is concentrated in the thin layer on the side from which measurement is made.

Materials containing TiO$_2$ coated on the reagent layer as the radiation-blocking layer do not require that the metal oxide or salt be added to the reagent layer as the lake dye-forming agent or that a component layer of the oxide or salt be provided. In this case, TiO$_2$ in the radiation-blocking or light-reflecting layer supplies the lake forming metal.

Embodiments of the multi-layered, chemical analysis material of the present invention for analyzing aqueous liquids are described below by reference to schematic views shown in FIGS. 1 to 3.

In FIG. 1, a single reagent layer 21 containing a lake dye precursor, urease, a lake forming metal salt or oxide which does not substantially inhibit urease activity, and a buffering agent dispersed in a hydrophilic binder is provided on light-transmitting, water-impermeable support 11. Radiation-blocking layer 41 and porous, sample-spreading layer 31 are provided in this sequence on the reagent layer 21 with respect to support 11.

When a drop of blood is applied to the sample-spreading layer in the direction indicated by A, the drop of blood uniformly spreads (in about the same volume per unit area) to reagent layer 21, where urea in the blood is decomposed to ammonia by the urease. The thus produced ammonia changes the color of the lake dye precursor to form a lake dye in proportion to the amount of ammonia produced. The degree of coloration of the thus formed lake dye is measured from the side indicated by B to determine urea.

Figure 2:
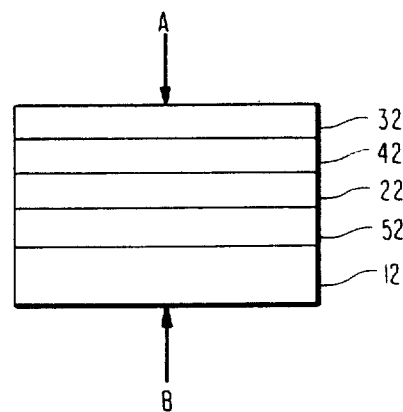
Figure 3:
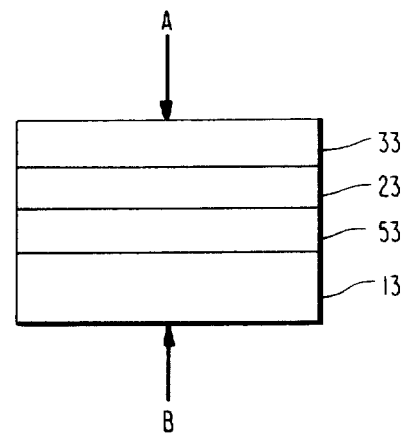

FIGS. 2 and 3 show other embodiments wherein the lake forming metal salt or oxide which does not substantially inhibit urease activity is provided as an independent layer. FIG. 2 shows an embodiment comprising light-transmitting, water-impermeable support 12 having provided thereon, in sequence, a layer of lake forming metal salt or oxide 52, reagent layer 22 containing a lake dye precursor and urease, radiation-blocking layer 42, and porous, sample-spreading layer 32, and FIG. 3 shows an embodiment comprising light-transmitting, water-impermeable support 13 having provided thereon in sequence a layer of lake forming metal salt or oxide 53, reagent layer 23 containing a lake dye precursor and urease, and porous, sample-spreading layer 33 also functioning as a radiation-blocking layer. As in FIG. 1, in both embodiments the drop of blood applied to the sample-spreading layer from direction A spreads to the reagent layer, where urea in the blood is decomposed to ammonia by the urease, and the degree of color formation of the lake dye formed from the lake dye precursor is measured from direction B to determine urea.

The present invention is described in more detail by reference to following examples which, however, are not to be construed as limiting the present invention in any way.

Unless otherwise indicated herein, all percentages, part, ratios and the like are by weight. All thicknesses set forth are dry thicknesses.

EXAMPLE 1

250 mg of haematoxylin dissolved in 0.5 ml of ethanol and 5 ml of water was added dropwise to a solution composed of 1 g of gelatin, 50 mg of Aerosol OT (tradename for a surface active agent: dioctyl sodium sulfosuccinate; made by Wako Junyaku Co., Ltd.), 50 mg of disodium ethylenediaminetetraacetate (EDTA.2NA), and 14 g of water to prepare a uniform solution. 80 mg of urease (made by Toyo Spinning Co., Ltd.; specific activity: 6 U/mg) was added thereto, and the resulting coating solution was coated on a 180-μm thick, colorless, transparent polyethylene terephthalate (PET) film in a dry thickness of about 7 μm to provide a reagent layer.

Then, a layer composed of titanium dioxide, gelatin, surface active agent (Aerosol OT) and water (weight ratio=34:13.4:0.18:240) was provided on the reagent layer in a thickness of 8 μm. Subsequently, a gelatin layer of a thickness of about 3 μm was provided thereon as an adhesive layer and, while in a wet condition, pressed onto a cotton broad cloth (made by Toyo Spinning Co., Ltd.; 100% cotton; 100 pairs) rendered hydrophilic with 0.2% Nonion HS 210 (tradename for a polyoxyethylene nonylphenoxy ether; made by Nippon Oils & Fats Co., Ltd.) to produce a multi-layered, chemical analysis sheet.

Blood urea nitrogen (BUN) standard solutions, prepared by adjusting the pH of 7% albumin solutions containing definite amounts of urea to 7.4 with a phosphate buffer solution, were dropped onto the above-described sheet in an amount of 10 μl per solution. After 10 minutes at 30° C., the optical reflection density in the central portion was measured using a Macbeth reflection densitometer, RD514 (maximum transmission wavelength: 600 nm).

The optical reflection densities versus various BUN concentrations were as tabulated in Table 1 below.

TABLE 1

| | BUN Concentration (mg/dl) | | | | | | | | |
|---|---|---|---|---|---|---|---|---|---|
| | 5 | 10 | 15 | 20 | 25 | 40 | 50 | 75 | 100 |
| Optical | 0.30 | 0.38 | 0.48 | 0.58 | 0.67 | 0.96 | 1.19 | 1.55 | 1.70 |

TABLE 1-continued

| | BUN Concentration (mg/dl) | | | | | | | |
|---|---|---|---|---|---|---|---|---|
| | 5 | 10 | 15 | 20 | 25 | 40 | 50 | 75 | 100 |
| Density | | | | | | | | | |

EXAMPLE 2

250 mg of haematoxylin dissolved in a solution composed of a mixture of 0.25 ml of ethanol and 0.24 ml of $C_{11}H_{23}CON(C_2H_5)_2$ was added to an aqueous solution (11.5 ml) containing 1 g of gelatin, 50 mg of a surface active agent (Aerosol OT), 100 mg of urease, and 50 mg of EDTA.2Na and, after emulsification and dispersion using an ultrasonic emulsifier, NS 250 (made by Hino Seiki K. K.), was coated on a 180-μm thick, colorless, transparent polyethylene terephthalate film in a dry thickness of about 7 μm. Subsequently, a titanium dioxide layer, an adhesive layer, and a sample-spreading layer were provided in this order on the above-described layer in the same manner as described in Example 1 to produce a multi-layered, chemical analysis sheet.

EXAMPLE 3

80 mg of urease was added to an aqueous solution (14 g) containing 1 g of gelatin, 50 mg of surface active agent (Aerosol OT), 50 mg EDTA.2Na), and 50 mg of iron sodium ethylenediaminetetraacetate (EDTA.-Fe(III).Na). Then, 250 mg of haematoxylin in 0.5 ml of ethanol was added thereto, and the resulting solution was coated on a 180-μm thick, colorless, transparent polyethylene terephthalate (PET) film in a dry thickness of about 7 μm. After drying, the same coating procedures as described in Example 1 were conducted to produce a multi-layered, chemical analysis sheet.

EXAMPLE 4

Using the procedures described in Example 3 a 150-μm thick layer (Micro Filter FM500; made by Fuji Photo Film Co., Ltd.) was pressed under moistening conditions to thereby provide a porous, sample-spreading layer. Thus, a multi-layered, chemical analysis sheet was produced.

EXAMPLE 5

An aqueous solution containing 20 g of gelatin, 0.1 g of surface active agent (Aerosol OT), and 0.4 g of EDTA.Fe(III).Na was coated on a 180-μm thick, colorless, transparent polyethylene terephthalate (PET) film in a dry thickness of about 7 μm to form a first layer. Then, a solution composed of 1 g of gelatin, 0.05 g of EDTA.2Na, 0.08 g of urease, 0.125 g of haematoxylin, 0.5 g of ethanol, and 10.5 g of water was coated on the first layer in a dry thickness of about 12 μm to form a second layer. A titanium dioxide layer (8 μm thick) and an adhesive layer (3 μm thick) were provided in sequence on the second layer in the same manner as described in Example 1, and the same type of cotton broad cloth as in Example 1 was further provided thereon to produce a multi-layer, chemical analysis sheet.

10 μl of fresh heparinized blood was dropped on a piece of the thus obtained multi-layered, chemical analysis sheet and, after incubation at 30° C. for 10 minutes, the optical reflection density was measured in the same manner as described in Example 1 to be 0.42.

Separately, 10 μl of blood plasma obtained by centrifuging the above-described heparinized blood was dropped on the same test piece, and the optical reflection density was measured in the same manner as described in Example 1 after incubation for 10 minutes to be 0.46.

EXAMPLE 6

On a gelatin-undercoated, 180-μm thick, colorless, transparent polyethylene terephthalate (PET) film was coated a coating solution composed of 1 g of gelatin, 400 mg of EDTA.Fe(III).Na, and 10 ml of water in a dry thickness of 2 μm to form a first layer. Then, a coating solution prepared by dissolving 1 g of gelatin, 50 mg of active agent (Aerosol OT), 250 mg of EDTA.2Na, 110 mg of EDTA.4Na, and 63 mg of haematoxylin in 10 ml of water was coated on the first layer in a dry thickness of 10 μm to form a second layer. Further, 80 mg of urease (made by Toyo Spinning Co., Ltd., specific activity: 6U/mg) was added to a coating solution composed of $TiO_2$, gelatin, surface active agent (Aerosol OT), and water (weight ratio=34:13.4:0.18:240), and coated on the second layer in a dry thickness of 8 μm. Then, an adhesive layer composed of a gelatin layer having a dry thickness of 3 μm was provided thereon, followed by providing thereon a sample-spreading layer composed of broad cloth (100 pairs) rendered hydrophilic in the same manner as in Example 1 to complete a multi-layered, chemical analysis sheet.

EXAMPLE 7

A multi-layered, chemical analysis sheet was produced in the same manner as described in Example 1 except that a broad cloth obtained by weaving mixed yarn of 60 count cotton yarn and polyester (PET) fiber (cotton fraction: 35% polyester fraction: 65%) was used in place of the cotton broad cloth. Using the thus produced multi-layered chemical analysis sheet, the same testing as in Example 1 was carried out whereby the same results as in Example 1 were obtained.

While the invention has been described in detail and with reference to specific embodiments thereof, it will be apparent to one skilled in the art that changes and modifications can be made therein without departing from the spirit and scope of the invention.

What is claimed is:

1. A multi-layered, chemical analysis element for analysis of an aqueous liquid, which comprises:
   (a) a light-transmitting, water impermeable support having provided thereon in sequence and without any intermediate layer;
   (b) a reagent layer; and
   (c) a porous, sample-spreading layer; with
      (i) said reagent layer (b) containing a lake dye precursor dispersed in a hydrophilic biner, wherein said lake dye precursor is haematoxylin, brazilin, dithizone, diphenylcarbazide, oxine, rubeanic acid, formaldoxime, dimethylglyoxime, alizarin, or sodium rhodinate,
      (ii) urease incorporated in the reagent layer (b) or in a layer immediately adjacent the reagent layer (b), and
      (iii) a member selected from the group consisting of a lake forming metal salt and a lake forming metal oxide selected from the group consisting of $TiO_2$, $SiO_2$, $Al_2O_3$ and an EDTA metal salt, incorporated in at least one of the reagent layer (b) and a layer immediately adjacent the reagent layer (b).

2. The chemical analysis element of claim 1, wherein said light-transmitting, water-impermeable support is a synthetic resin film, a film of regenerated cellulose or a glass plate.

3. The chemical analysis element of claim 1, wherein said porous, sample-spreading layer is a layer of a fabric comprised of natural fibers, synthetic fibers or mixtures thereof.

4. The chemical analysis element of claim 3, wherein said fabric is one subjected to a treatment rendering such hydrophilic.

5. The chemical analysis element of claim 1, wherein said porous, sample-spreading layer is a layer of a non-fibrous, isotropic, porous material.

6. The chemical analysis element of claim 1, wherein said lake dye precursor is haematoxylin.

7. The chemical analysis element of claim 1, wherein said element is such that color reaction in said chemical analysis element occurs at a pH of about 6.5 or higher.

8. The chemical analysis element of claim 1, wherein said hydrophilic binder is a water-soluble high molecular weight polymer.

9. The chemical analysis element of claim 8, wherein said high molecular weight polymer is a water-soluble protein, a vegetable gum or a synthetic polymer.

10. The chemical analysis element of claim 1, wherein said element additionally contains in said reagent layer or another layer thereof at least one of a stabilizer and a buffer.

11. The chemical analysis element of claim 1, wherein at least one of urease, said lake forming metal salt or said lake forming metal oxide is incorporated in a layer directly adjacent to the reagent layer (b).

12. The chemical analysis element of claim 1, wherein said EDTA salt is selected from Fe(III) salt of EDTA and Na salt of EDTA.

13. The chemical analysis element of claim 1, wherein said lake forming metal salt or said lake forming metal oxide are present in the layer which is adjacent said reagent layer (b).

14. The chemical analysis element of claim 1, wherein said reagent layer (b) and said porous, sample-spreading layer (c) are hydrophilic layers.

15. The chemical analysis element of claim 1, wherein said porous, sample spreading layer contains a radiation-blocking powder.

16. A multi-layered, chemical analysis element for analysis of an aqueous liquid, which comprises:
(a) a light-transmitting, water impermeable support having provided thereon in sequence and without any intermediate layer;
(b) a reagent layer;
(c) a radiation-blocking layer; and
(d) a porous, sample spreading layer;
  (i) said reagent layer (b) containing a lake dye precursor dispersed in a hydrophilic binder, wherein said lake dye precursor is haematoxylin, brazilin, dithizone, diphenylcarbazide, oxine, rubeanic acid, formaldoxime, dimethylglyoxime, alizarin, or sodium rhodinate,
  (ii) urease incorporated in the reagent layer (b) or in a layer immediately adjacent the reagent layer (b), and
  (iii) a member selected from the group consisting of a lake forming metal salt and a lake forming metal oxide selected from the group consisting of $TiO_2$, $SiO_2$, $Al_2O_3$ and an EDTA metal salt, incorporated in at least one of the reagent layer (b) and a layer immediately adjacent the reagent layer (b).

17. The chemical analysis element of claim 16, wherein said light-transmitting, water-impermeable support is a synthetic resin film, a film of regenerated cellulose or a glass plate.

18. The chemical analysis element of claim 16, wherein said porous, sample-spreading layer is a layer of a fabric comprised of natural fibers, synthetic fibers or mixtures thereof.

19. The chemical analysis element of claim 18, wherein said fabric is one subjected to a treatment rendering such hydrophilic.

20. The chemical analysis element of claim 16, wherein said porous, sample-spreading layer is a layer of a non-fibrous, isotropic, porous material.

21. The chemical analysis element of claim 16, wherein said lake dye precursor is haematoxylin.

22. The chemical analysis element of claim 16, wherein said element is such that color reaction in said chemical analysis material occurs at a pH of about 6.5 or higher.

23. The chemical analysis element of claim 16, wherein said hydrophilic binder is a water-soluble high molecular weight polymer.

24. The chemical analysis element of claim 23, wherein said high molecular weight polymer is a water-soluble protein, a vegetable gum or a synthetic polymer.

25. The chemical analysis element of claim 16, wherein said element additionally contains in said reagent layer or another layer thereof at least one of a stabilizer and a buffer.

26. The chemical analysis element of claim 16, wherein said element comprises, in order from said light-transmitting, water-impermeable support, said reagent layer containing a lake dye precursor, urease, a lake forming metal salt or oxide and a buffering agent, said radiation blocking layer and said porous, sample-spreading layer.

27. The chemical analysis element of claim 16, wherein at least one of urease, said lake forming metal salt or said lake forming metal oxide is incorporated in a layer directly adjacent to the reagent layer (b).

28. The chemical analysis element of claim 16, wherein said EDTA salt is selected from Fe(III) salt of EDTA and Na salt of EDTA.

29. The chemical analysis element of claim 16, wherein said lake forming metal salt or said lake forming metal oxide are present in the layer which is adjacent said reagent layer (b).

30. A multi-layered, chemical analysis element for analysis of an aqueous liquid, which comprises:
(a) a light-transmitting, water impermeable support having provided thereon in sequence and without any intermediate layer;
(b) a layer of a member selected from the group consisting of a lake forming metal salt and a lake forming metal oxide selected from the group consisting of $TiO_2$, $SiO_2$, $Al_2O_3$ and an EDTA metal salt;
(c) a reagent layer; and
(d) a radiation blocking layer; and
(e) a porous, sample-spreading layer; with
  (i) said reagent layer (c) containing a lake dye precursor dispersed in a hydrophilic binder, wherein said lake dye precursor is haematoxylin, brazilin, dithizone, diphenylcarbazide, oxine, rubeanic acid, formaldoxime, dimethylglyoxime, alizarin, or sodium rhodinate, and
  (ii) urease incoporated in the reagent layer (c) or in a layer immediately adjacent the reagent layer (c).

31. A multi-layered, chemical anaylsis element for analysis of an aqueous liquid, which comprises
  (a) a light-transmitting, water impermeable support having provided thereon in sequence and without any intermediate layer;
  (b) a layer of a member selected from the group consisting of a lake forming metal salt and a lake forming metal oxide selected from the group consisting of $TiO_2$, $SiO_2$, $Al_2O_3$ and an EDTA metal salt;
  (c) a reagent layer; and
  (d) a porous, sample-spreading layer; with
    (i) said reagent layer (c) containing a lake dye precursor dispersed in a hydrophilic binder, wherein said lake dye precursor is haematoxylin, brazilin, dithizone, diphenylcarbazide, oxine, rubeanic acid, formaldoxime, dimethylglyoxime, alizarin, or sodium rhodinate, and
    (ii) urease incorporated in the reagent layer (c) or in a layer immediately adjacent the reagent layer (c).

32. The chemical analysis element of claim 31, wherein said porous, sample spreading layer contains a radiation-blocking powder.

33. A multi-layered, chemical analysis element for analysis of an aqueous liquid, which comprises
  (a) a light-transmitting, water impermeable support having provided thereon in sequence and without any intermediate layer;
  (b) a reagent layer;
  (c) an adhesive layer; and
  (d) a porous, sample-spreading layer; with
    (i) said reagent layer (b) containing a lake dye precursor dispersed in a hydrophilic binder, wherein said lake dye precursor is haematoxylin, brazilin, dithizone, diphenylcarbazide, oxine, rubeanic acid, formaldoxime, dimethylglyoxime, alizarin, or sodium rhodinate,
    (ii) urease incoporated in the reagent layer (b) or in a layer immediately adjacent the reagent layer (b), and
    (iii) a member selected from the group consisting of a lake forming metal salt and a lake forming metal oxide selected from the group consisting of $TiO_2$, $SiO_2$, $Al_2O_3$ and an EDTA metal salt, incorporated in at least one of the reagent layer (b) and a layer immediately adjacent the reagent layer (b).

34. A multi-layered, chemical analysis element for analysis of an aqueous liquid, which comprises:
  (a) a light-transmitting, water impermeable support having provided thereon in sequence and without any intermediate layer;
  (b) a reagent layer;
  (c) a radiation-blocking layer,
  (d) an adhesive layer; and
  (e) a porous, sample-spreading layer; with
    (i) said reagent layer (b) containing a lake dye precursor dispersed in a hydrophilic binder, wherein said lake dye precursor is haematoxylin, brazilin, dithizone, diphenylcarbazide, oxine, rubeanic acid, formaldoxime, dimethylglyoxime, alizarin, or sodium rhodinate,
    (ii) urease incorporated in the reagent layer (b) or in a layer immediately adjacent the reagent layer (b), and
    (iii) a member selected from the group consisting of a lake forming metal salt and a lake forming metal oxide selected from the group consisting of $TiO_2$, $SiO_2$, $Al_2O_3$ and an EDTA metal salt, incorporated in at least one of the reagent layer (b) and a layer immediately adjacent the reagent layer (b).

35. A multi-layered, chemical analysis element for analysis of an aqueous liquid, which comprises:
  (a) a light-transmitting, water impermeable support having provided thereon in sequence and without any intermediate layer;
  (b) a reagent layer;
  (c) a layer of a member selected from the group consisting of a lake forming metal salt and a lake forming metal oxide selected from the group consisting of $TiO_2$, $SiO_2$, $Al_2O_3$ and an EDTA metal salt;
  (d) a radiation-blocking layer; and
  (e) a porous, sample-spreading layer; with
    (i) said reagent layer (b) containing a lake dye precursor dispersed in a hydrophilic binder, wherein said lake dye precursor is haematoxylin, brazilin, dithizone, diphenylcarbazide, oxine, rubeanic acid, formaldoxime, dimethylglyoxime, alizarin, or sodium rhodinate, and
    (ii) urease incorporated in the reagent layer (b) or in a layer immediately adjacent the reagent layer (b).

36. The chemical analysis element of claim 33, wherein said porous, sample spreading layer contains a radiation-blocking powder.

37. A multi-layered, chemical analysis element for analysis of an aqueous liquid, which comprises:
  (a) a light-transmitting, water impermeable support having provided thereon in sequence and without any intermediate layer;
  (b) a reagent layer;
  (c) a layer of a member selected from the group consisting of a lake forming metal salt and a lake forming metal oxide selected from the group consisting of $TiO_2$, $SiO_2$, $Al_2O_3$ and an EDTA metal salt; and
  (d) a porous, sample-spreading layer; with
    (i) said reagent layer (b) containing a lake dye precursor dispersed in a hydrophilic binder, wherein said lake dye precursor is haematoxylin, brazilin, dithizone, diphenylcarbazide, oxine, rubeanic acid, formaldoxime, dimethylglyoxime, alizarin, or sodium rhodinate, and
    (ii) urease incorporated in the reagent layer (b) or in a layer immediately adjacent the reagent layer (b).

38. The chemical analysis element of claim 37, wherein said porous, sample spreading layer contains a radiation-blocking powder.

39. A multi-layered, chemical analysis element for analysis of an aqueous liquid, which comprises:
  (a) a light-transmitting, water impermeable support having provided thereon in sequence and without any intermediate layer;
  (b) a reagent layer;
  (c) a layer of a member selected from the group consisting of a lake forming metal salt and a lake forming metal oxide selected from the group consisting of $TiO_2$, $SiO_2$, $Al_2O_3$ and an EDTA metal salt;
  (d) an adhesive layer; and (e) a porous, sample-spreading layer; with
  (i) said reagent layer (b) containing a lake dye precursor dispersed in a hydrophilic binder, wherein said lake dye precursor is haematoxylin, brazilin, dithizone, diphenylcarbazide, oxine, rubeanic acid, formaldoxime, dimethylglyoxime, alizarin, or sodium rhodinate, and
  (ii) urease incorporated in the reagent layer (b) or in a layer immediately adjacent the reagent layer (b).

40. The chemical analysis element of claim 39, wherein said porous, sample spreading layer contains a radiation-blocking powder.

41. A multi-layered, chemical analysis element for analysis of an aqueous liquid, which comprises
  (a) a light-transmitting, water impermeable support having provided thereon in sequence and without any intermediate layer;
  (b) a layer of a member selected from the group consisting of a lake forming metal salt and a lake forming metal oxide selected from the group consisting of $TiO_2$, $SiO_2$, $Al_2O_3$ and an EDTA metal salt;
  (c) a reagent layer;
  (d) an adhesive layer; and
  (e) a porous, sample-spreading layer; with
    (i) said reagent layer (c) containing a lake dye precursor dispersed in a hydrophilic binder, wherein said lake dye precursor is haematoxylin, brazilin, dithizone, diphenylcarbazide, oxine, rubeanic acid, formaldoxime, dimethylglyoxime, alizarin, or sodium rhodinate, and
    (ii) urease incorporated in the reagent layer (c) or in a layer immediately adjacent the reagent layer (c).

42. The chemical analysis element of claim 41, wherein said porous, sample spreading layer contains a radiation-blocking powder.

43. A multi-layered, chemical analysis element for analysis of an aqueous liquid, which comprises:
  (a) a light-transmitting, water impermeable support having provided thereon in sequence and without any intermediate layer;
  (b) a reagent layer;
  (c) a layer of a member selecteed from the group consisting of a lake forming metal salt and a lake forming metal oxide selected from the group consisting of $TiO_2$, $SiO_2$, $Al_2O_3$ and an EDTA metal salt;
  (d) a radiation-blocking layer;
  (e) an adhesive layer; and
  (f) a porous, sample-spreading layer; with
    (i) said reagent layer (b) containing a lake dye precursor dispersed in a hydrophilic binder, wherein said lake dye precursor is haematoxylin, brazilin, dithizone, diphenylcarbazide, oxine, rubeanic acid, formaldoxime, dimethylglyoxime, alizarin, or sodium rhodinate,
    (ii) urease incorporated in the reagent layer (b) or in a layer immediately adjacent the reagent layer (b).

44. A multi-layered, chemical analysis element for analysis of an aqueous liquid, which comprises:
  (a) a light-transmitting, water impermeable support having provided thereon in sequence and without any intermediate layer;
  (b) a layer of a member selected from the group consisting of a lake forming metal salt and a lake forming metal oxide selected from the group consisting of $TiO_2$, $SiO_2$, $Al_2O_3$ and an EDTA metal salt;
  (c) a reagent layer;
  (d) a radiation-blocking layer;
  (e) an adhesive layer; and
  (f) a porous, sample-spreading layer; with
    (i) said reagent layer (c) containing a lake dye precursor dispersed in a hydrophilic binder, wherein said lake dye precursor is haematoxylin, brazilin, dithizone, diphenylcarbazide, oxine, rubeanic acid, formaldoxime, dimethylglyoxime, alizarin, or sodium rhodinate, and
    (ii) urease incorporated in the reagent layer (c) or in a layer immediately adjacent the reagent layer (c).

* * * * *